United States Patent [19]

Holtkamp

[11] Patent Number: Plant 5,493

[45] Date of Patent: Jun. 18, 1985

[54] AFRICAN VIOLET PLANT NAMED ELLEN

[75] Inventor: Reinhold Holtkamp, Isselburg, Fed. Rep. of Germany

[73] Assignee: Gessellschaftsvertrag uber die Erfindergemeinschaft "Optimara", Rees Haffen, Fed. Rep. of Germany

[21] Appl. No.: 535,261

[22] Filed: Sep. 23, 1983

[51] Int. Cl.[3] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of African violet plant named Ellen characterized by its intensive pink flowers, which do not fade under high temperatures, upright flower stems which carry the flower bouquet centrally above the foliage, vigorous compact growth habit, and by its very long lasting flowers that are non-dropping.

1 Drawing Figure

The present invention comprises a new and distinct cultivar of African violet plant, botanically known as *Saintpaulia ionantha,* and named Ellen.

The new cultivar was referred to during the breeding and selection process by the designation G 91/5, and is a product of a planned breeding program.

The new cultivar was originated from a cross made in a controlled breeding program in Isselburg, West Germany. The female, or seed parent was a cultivar designated 40/78 pink single. The male parent, or pollen parent was a cultivar designated 47/78 pink girl.

The new cultivar Ellen was discovered and selected by me as a flowering plant within the progeny of the stated cross in a controlled environment in Isselburg, West Germany. Asexual reproduction of the new cultivar by leaf cuttings and by division of shoots, as performed by me at Isselburg, West Germany, has demonstrated that the combination of characteristics as herein disclosed for the new cultivar are firmly fixed and are retained through successive generations of asexual reproduction.

Ellen has not been observed under all possible environmental conditions. The phenotype may vary significantly with variations in environment such as temperature, light intensity and day length. The following observations, measurements and values describe the new cultivar as grown in Isselburg, West Germany and Nashville, Tenn., under greenhouse conditions which closely approximate those generally used in commercial practice.

The following traits have been repeatedly observed and are determined to be basic characteristics of Ellen, which in combination distinguish this African violet as a new and distinct cultivar:

(1) Vigorous compact growth habit.

(2) Intensive pink flower color which doesn't fade under high temperatures, and becomes even more intensive when grown under cooler conditions.

(3) Upright flower stems, which carry the flower bouquet above the foliage and at the center of the plant.

(4) The flowers are very long lasting and do not drop.

The accompanying photographic drawing shows a typical specimen plant of the new cultivar. The colors appearing in the photograph are as true as possible with color illustrations of this type.

In the following description, color references are made to Royal Horticultural Society Colour Chart (R.H.S.) except where general colors of ordinary significance are referred to. Color values were taken under natural light conditions at approximately 2:00 P.M. in early September in Nashville, Tenn.

Botanical classification: *Saintpaulia ionantha,* Ramat. cv ELLEN.

Parentage:

*Male parent.*—47/78 pink girl.

*Female parent.*—40/78 pink single.

Propagation: The new cultivar holds its distinguishing characteristics through successive propagations by leaf cuttings and by division of shoots.

Plant: From 6 cm. to 8 cm. tall when grown in pots, and approximately 20–25 cm. in diameter when fully grown.

Leaves:

*Diameter.*—5 cm. wide and up to 6½cm. long.

*Texture.*—Leather-like.

*Aspect.*—Slightly hairy.

*Veins.*—Visable, well pronounced under side.

*Color (upperside).*—Green group 137A.

*Color (underside).*—Yellow green 148D.

*Petiole.*—Purplish red, hairy.

Flowers:

*Buds.*—Ball shaped.

*Sepals.*—Greenish brown, light green tips, hairy; turning to beige purple. Calyx: Dark brown. Aspect: Hairy. Peduncle: Greenish brown.

Individual flowers:

*Size.*—40–45 mm.

*Color.*—Upperside: Red purple 68A-B, center slightly darker. Underside: Red purple 73B.

*Borne.*—On very upright stems, carrying up to 6–9 frilled flowers.

*Shape.*—Violet shape.

*Flowering time.*—8–10 weeks before flower bouquet.

Reproductive organs:

*Anthers.*—Two cells.

*Filaments.*—Light green.

*Styles.*—Pink with darker tip; light green base and hairy.

Roots: Normal developed, white and hairy when active, changing to brownish when older.

Disease resistance: Good as experienced to date.

General observations: The variety Ellen is a vigorous and compact African violet which has intensive pink flower color. The color does not fade under higher temperatures, and becomes even more intensive when grown under cooler conditions. The flower stems are upright at the center of the plant and carry the flower bouquet well above the foliage. The flowers are very long lasting and dry on the stems, as opposed to dropping off.

I claim:

1. A new and distinct cultivar of African violet plant named Ellen, as described and illustrated, and particularly characterized by its intensive pink flowers which do not fade under high temperatures, upright flower stems which carry the flower bouquet centrally above the foliage, vigorous compact growth habit, and by its very long lasting flowers that are non-dropping.

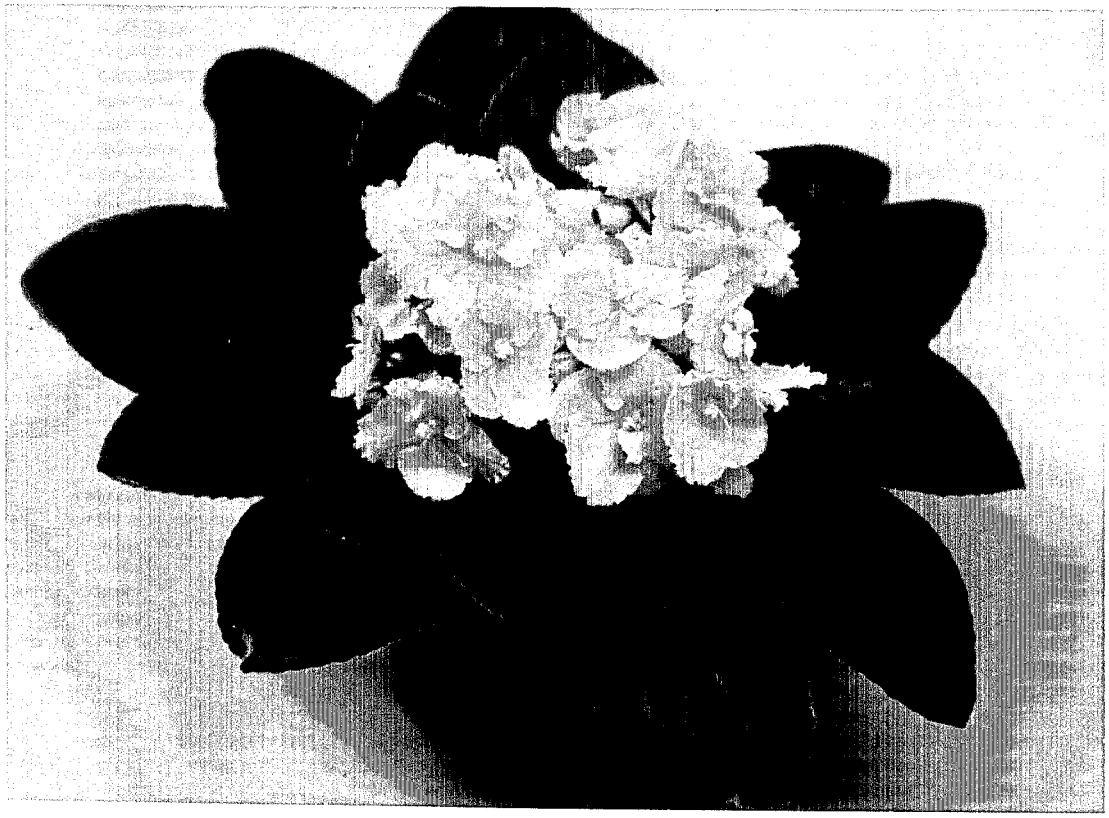

* * * * *